United States Patent [19]
Shim

[11] 3,969,437
[45] July 13, 1976

[54] CYCLIC PHOSPHORUS ESTERS

[75] Inventor: Kyung Sup Shim, Irvington, N.Y.

[73] Assignee: Stauffer Chemical Company, Westport, Conn.

[22] Filed: Feb. 23, 1971

[21] Appl. No.: 118,164

[52] U.S. Cl............................ 260/937; 260/2.5 AJ; 428/276
[51] Int. Cl.²........................ C07F 9/40; C08J 9/00
[58] Field of Search..................................... 260/937

[56] References Cited
UNITED STATES PATENTS

| | | | |
|---|---|---|---|
| 3,134,742 | 5/1964 | Wismer et al................... | 260/945 X |
| 3,597,503 | 8/1971 | Wilson et al....................... | 260/937 |

*Primary Examiner*—Anton H. Sutto
*Attorney, Agent, or Firm*—Richard P. Fennelly

[57] ABSTRACT

Novel cyclic phosphorus esters are disclosed having the formula:

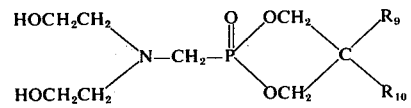

where $R_9$ and $R_{10}$ can be the same or different and are selected from the group consisting of hydrogen, lower alkyl, lower hydroxyalkyl, lower haloalkyl and hydroxy with the proviso that no more than one of $R_9$ and $R_{10}$ can be hydroxy. These compounds are useful for the preparation of flame retardant textile finishes as well as for use as polyols for preparing flame retardant polyurethane foams.

3 Claims, No Drawings

CYCLIC PHOSPHORUS ESTERS

This invention relates to a novel class of cyclic phosphorus esters which are especially suited for use in preparing flame retardant textile finishes. More particularly, this invention relates to the preparation and use of these novel cyclic esters in a process for flame retarding textiles which comprises passing the textile through an aqueous padding solution containing one of these esters along with dimethyloldihydroxyethylene urea and an acid curing catalyst and thereafter curing the treated textile to render the textile flame retardant. The present process is useful for flame retarding various types of textiles, especially cellulosic, including cotton and polyester-cotton blends, viscose rayon, jute, and products made from wood pulp.

By textile is meant hereinafter a fabric, filament, staple, or yarn, or product made therefrom, which may be woven or non-woven.

The flame retarding of textiles is of importance for improvement of the safety characteristics of apparel, bedding, protective clothing, tent cloth, carpets, home furnishings, aircraft and automobile interior fabrics, and industrial fabrics which may be woven, knitted, tufted and non-woven.

There are various methods known for flame retarding textiles which include the application of chlorinated paraffins with antimony oxide or tris-(dibromopropyl phosphate) plus a resinous binder. Such procedures generally have the disadvantage of requiring the addition of a large amount of solids with a resulting deleterious effect in the quality of the fabric. Furthermore, the resulting finishes are quite limited in their durability to laundering and dry-cleaning. There have been finishes designed to be especially durable for cotton, for example, those based on tetrakis (hydroxymethyl) phosphonium chloride or on phosphonated N-methylolamides, but these have various limitations.

The tetrakis (hydroxymethyl) phosphonium chloride finishes have problems with odor (formaldehyde and phosphine-like odors), and stiffness, i.e., a poor "hand". Attempts to overcome the hand problem by use of ammonia gas as a curing reagent have required equipment not generally available in textile mills. The phosphonated N-methylolamide finishes have been found in mill practice to have problems of volatility, loss of phosphorus in the pad-dry-cure afterwash cycle, and ultraviolet or thermal stability limitations.

A further major limitation of the known finishes is their ineffectiveness on cotton-polyester blends, which are fabrics of great commercial importance.

It is therefore a very important object of the present invention to make available flame retardant finishes which can be used on natural and synthetic textiles and fabrics, especially on cellulosics and cellulosic - synthetic blends, which involves the use of substantially non-toxic, less-volatile phosphorus compounds, and which leaves the fabric with a soft tactile character (i.e., good "hand") and good physical strength properties.

It is a further object to make available textile finishes which are durable to both washing and drycleaning as well as being flame retardant.

Another object of the present invention is to make available finishes useful for cotton-synthetics, especially cotton-polyester blends.

Another object of the present invention is to provide a process that can be used with the primary polyol phosphonate to prevent undesirable color development on textiles. Those primary polyol phosphonates, such as O,O-diethyl N,N-bis(2-hydroxyethyl)aminomethyl phosphonate, that may develop some color on curing can be whitened with a prolonged bleaching operation. Prior to this invention, this whitening process involved bleaching the treated textile for at least 20 minutes in a 5% solution of sodium perborate at 180°F.

According to the present invention, it has been unexpectedly found that by adding sodium perborate to the padding solution and then padding and curing the solution on the textile, the color is essentially prevented from forming on the textiles.

Also, according to the present invention, it has been unexpectedly found that dimethyloldihydroxyethylene urea provides good reactivity and durability with the above primary polyol phosphonates whereas aminoplasts such as dimethylolethylene urea and methylolated melamines do not.

The present invention primarily provides a process for flame retarding most textiles with a finish which can be thermally cured, a finish which is durable when the textile is washed or dry cleaned, and which finish does not cause a color loss or undesired color development to the flame retardant textile.

The present flame retarding process comprises applying to a textile an aqueous solution containing a primary polyol phosphonate, dimethyloldihydroxyethylene urea, and an acid or latent acid catalyst. The aqueous bath may also contain optionally other aminoplast resins, softeners, surfactants, and bleaching agents. Then, the solution is dried on the fabric and the primary polyol phosphonate and dimethyloldihydroxyethylene urea are cured on the textile by heating means to render the textile flame retardant. By "curing," is meant the formation of a water-insoluble presumably polymeric finish by the co-reaction of the phosphorus alcohol and the dimethyloldihydroxyethylene urea. Where cellulose is the substrate chemical bonding to the cellulose may also be involved to an unknown degree.

The phosphorus reactant to be used in the process of the invention must contain at least one carbon-bonded primary alcohol group plus a pentavalent phosphorus ester group. Secondary alcohol groups do not lead to durable finishes.

By a carbon-bonded primary alcohol group is meant a ($HOCH_2$—) group attached to a carbon atom, which can be a methylene, methine, or quaternary carbon atom. This structure is to be contrasted with methylol groups attached to nitrogen or phosphorus, which have distinctly different chemistry from the methylol groups on carbon.

In particular, the alcohol groups required by the process of the invention are those which do not revert to formaldehyde in contrast to the methylol groups such as N-methylol amides or tetrakis (hydroxymethyl) phosphonium salts which are known to be in equilibrium with formaldehyde or which can release formaldehyde. Not being capable of releasing formaldehyde, the reactant alcohol compounds as used in the process of the invention do not lead to an undesirable degree of cross-linking of the cellulosic fibers with ensuing stiff hand and loss of abrasion resistance or tear strength.

By a pentavalent phosphorus ester group is meant a structure of the general formula:

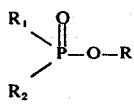

$$\begin{matrix} R_1 \\ \phantom{R} \\ R_2 \end{matrix} \!\!\! \begin{matrix} O \\ \| \\ P-O-R \end{matrix} \qquad (I)$$

where R is a hydrocarbyl radical, preferably an aliphatic group of 1 to 20 carbon atoms, which may be unsubstituted or substituted by hydroxy and or halogen. The remaining two valences of the phosphorus are satisfied by other organic radicals $R_1$ and $R_2$ such, for example, as alkyl and alkoxy which may be unsubstituted or substituted by alkoxy, halogen or hydroxy groups; hydroxypolyalkyleneoxy; phenyl; halophenyl; amino-substituted alkyl; —O— alkylene—O— or —O—alkyleneoxyalkylene—O— bonded to the same or to another pentavalent phosphorus ester group; amino; alkyl-substituted amino or hydroxyalkyl-substituted amino, all with the proviso that in at least one of the aforementioned groups there be at least one carbon-bonded primary alcohol group.

It is preferred, for reasons of improved durability, to have two or more carbon-bonded primary alcohol groups in the phosphorus reagent, and for reasons of avoiding excessive cross linking, to have no more than six such groups in the molecule.

Where the term alkyl, alkoxy, or alkylene is employed, it is preferred to have no more than eight carbon atoms in the radical, hereinafter designated lower alkyl, lower alkoxy, or lower alkylene.

The following compounds (Formula II) are examples of a subgroup of useful pentavalent phosphorus esters according to the present invention having the formula:

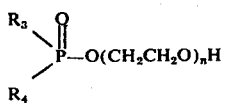

$$\begin{matrix} R_3 \\ \phantom{R} \\ R_4 \end{matrix} \!\!\! \begin{matrix} O \\ \| \\ P-O(CH_2CH_2O)_nH \end{matrix} \qquad (II)$$

wherein $R_3$ and $R_4$ are selected from the group consisting of lower alkyl, halogenated lower alkyl, lower alkoxyalkyl, lower hydroxyalkyl, lower alkoxy, lower hydroxyalkoxy, and halogenated lower alkoxy, hydroxypolyalkyleneoxy; and n is an integer from 1 to 6.

These compounds have good color and are generally convenient to synthesize from low cost materials such as by reaction of ethylene oxide with acid phosphates, pyrophosphates and phosphoric acid. Compounds of this class include the primary alcohols described in U.S. Pat. Nos. 2,372,244; 3,402,132; 3,474,046; 3,474,047; and 3,487,030; and British Pat. No. 1,082,013; which patents describe the synthesis and other uses for these compounds.

An example of this subgroup of pentavalent phosphorus esters is the compound:

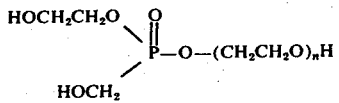

$$\begin{matrix} HOCH_2CH_2O \\ \phantom{R} \\ HOCH_2 \end{matrix} \!\!\! \begin{matrix} O \\ \| \\ P-O-(CH_2CH_2O)_nH \end{matrix} \qquad (III)$$

where n has a value of from about 3 to 5. This compound is sold under the tradename of FYROL HMP, by the Stauffer Chemical Company.

A particularly useful group of phosphonates having carbon-bonded primary alcohol groups and suitable for the present invention include various phosphorus derivatives of diethanolamine having the general formula:

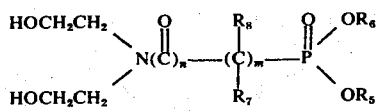

wherein $R_5$ and $R_6$ are alkyls, hydroxyalkyls, haloalkyls, alkoxyalkyls or hydroxyalkoxyalkyls of 1 to 6 carbon atoms, the termini of an alkylene forming a six-membered ring or halogenated analogs, the termini of an alkylene or alkyleneoxyalkylene bonded to a like phosphorus ester group, hydroxypolyoxyalkylene or hydroxy-substituted analogs thereof; $R_7$ and $R_8$ are hydrogen, lower alkyls of 1 to 6 carbon atoms; $m$ is an integer from 0 to 2; and $n$ is an integer from 0 to 1.

Examples of the phosphorus derivatives of this group include the following:

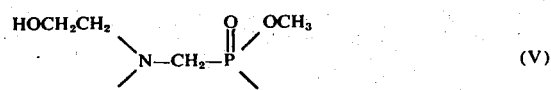

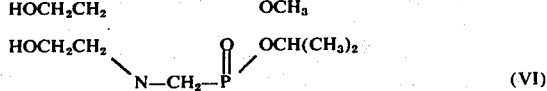

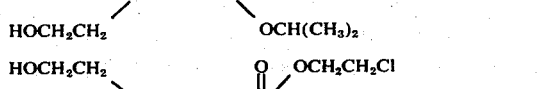

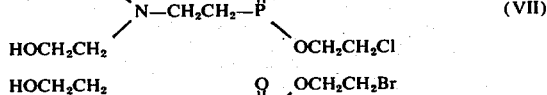

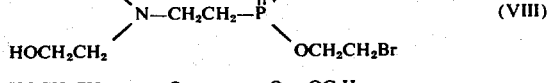

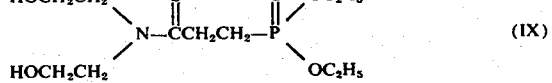

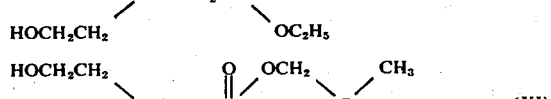

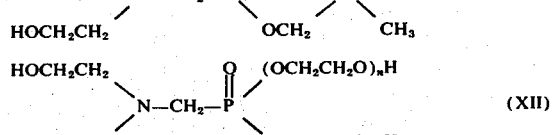

where $n$ is an integer from 1 to 10.

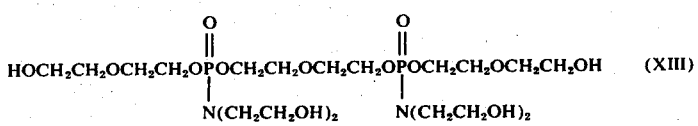

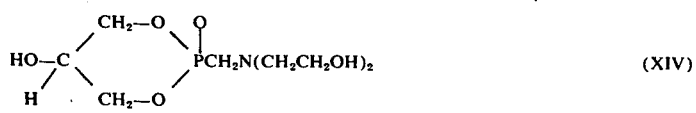
(XIV)

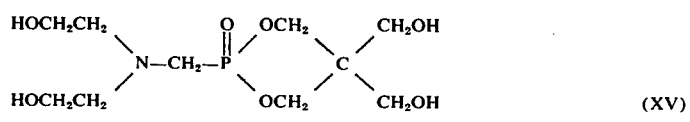
(XV)

(XVI)

(XVII)

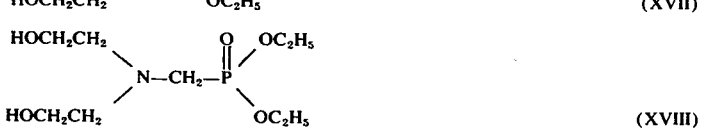
(XVIII)

These compounds constitute a preferred subgroup within the invention, since they generally impart a higher degree of flame retardance relative to their phosphorus content, than do the nonamine derived compounds within the broader scope of the invention. Their synthesis and use for other purposes are described in U.S. Pat. Nos. 3,076,010; 3,475,333; and 3,294,710; and British Pat. No. 1,178,718.

A narrow preferred subgroup of pentavalent phosphorus esters, because of the ease of their manufacture, stability, and good flame retardant efficacy is:

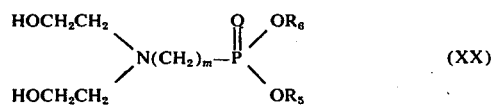
(XX)

where $m$ is an integer from 0 to 2 and $R_5$ and $R_6$ are defined hereinabove.

A preferred group of pentavalent phosphorus esters, because of their unusually favorable color, stability, and flame retardant efficacy are:

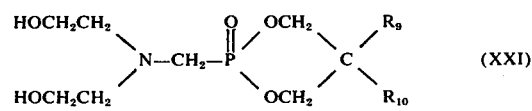
(XXI)

where $R_9$ and $R_{10}$ can be the same or different and are selected from the group consisting of hydrogen, lower alkyl, lower hydroxyalkyl, lower haloalkyl and hydroxy with the proviso that no more than one of $R_9$ and $R_{10}$ can be hydroxy. The preferred lower alkyl group in the applicable alkyl, hydroxyalkyl or haloalkyl groups is the methyl radical.

This class of compounds, all of which are new compositions of matter, can be readily prepared by reacting the known cyclic phosphonate of 2,2-dimethylpropane-1,3-diol, or an appropriately substituted derivative of the latter diol where it is desired to vary $R_9$ and/or $R_{10}$, with diethanolamine and formaldehyde in the manner described in U.S. Pat. No. 3,076,010. Alternatively, the diethanolamine and formaldehyde may be replaced in this reaction with hydroxyethyl oxazolidine.

In general, the conditions for this reaction involve adding the diethanolamine to the formaldehyde, with agitation, at a temperature in the range of about 20°–30°C. Thereafter, the cyclic phosphonate of 2,2-dimethylpropane-1,3-diol, or a substituted derivative thereof, is introduced with agitation at a temperature in the range of from about 20°–90°C. This reaction is exothermic so that the mixture is held at the latter temperature until all of the phosphonate has reacted. The desired end product is then recovered by removal of water. Where hydroxyethyl oxazolidine is used in place of the formaldehyde and diethanolamine, it is simply combined with the cyclic phosphonate under the above described reaction conditions.

Exemplary of this preferred group of pentavalent phosphorus esters are the compounds:

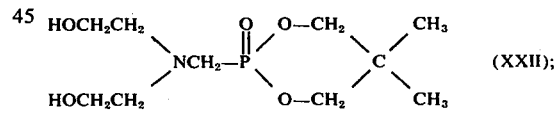
(XXII);

(XXIII);

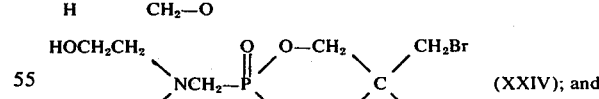
(XXIV); and

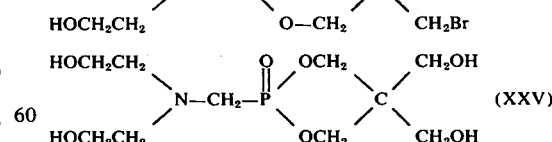
(XXV)

It may also be noted that the above described class of compounds can be used as polyols in the preparation of polyesters and polyurethanes.

The most preferred phosphonate for use in the present invention because of its excellent flame retardant efficacy is the compound:

O,O-diethyl N,N-bis(2-hydroxy ethyl) aminomethylphosphonate which compound is sold under the tradename "Fyrol 6", by the Stauffer Chemical Company.

The process of the present invention is based upon the finding that dimethyloldihydroxyethylene urea which co-cured with a phosphorus compound of the above-defined type, imparts durable flame retardancy to the textile, good tactile quality (hand), and good physical strength properties.

The compound dimethyoldihydroxyethylene urea, hereinafter known as DMDHEU, has the structure:

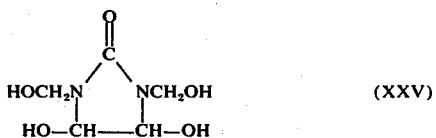

(XXV)

and is well known in the textile finishing art as a durable press finishing resin. DMDHEU is synthesized by the reaction of glyoxal with urea followed by methylolation of the resultant dihydroxyethylene urea with formaldehyde. Similar materials such as dimethylolethylene urea exhibit poor durability with the above described primary alcohols.

The acid curing catalyst for the process of the present invention may be any compound which affords an acidic reaction at the curing temperature. Such catalysts include mineral acids such as hydrochloric and phosphoric, organic acids such as oxalic, citric, succinic, maleic, glycolic, chloroacetic, and trichloroacetic, toluenesulfonic, alkyl acid phosphates and the like. Also included are the salts of strong acids with relatively weak bases, for example zinc chloride, magnesium chloride, ammonium chloride, ammonium phosphates, and amine hydrochlorides. Some typical amine hydrochlorides include 2-amino-2-methylpropanol hydrochloride, sold under the tradename "Catalyst AC", by the Monsanto Chemical Company, and the alkanolamine hydrochloride sold as "Catalyst XRF", by the Millmaster Onyx Corporation. A preferred salt catalyst is a buffered zinc nitrate catalyst, sold under the tradename "Catalyst X-4", by the Sun Chemical Company.

It is to be understood that the above mentioned salts may be viewed as "latent" acid catalysts, which do not have substantial acid properties at low temperatures but which become acid, by hydrolysis or dissociation, at the curing temperature of the phosphonate and DMDHEU on the textile.

The pH of the paddng bath is preferably adjusted to a pH of between about 3 and about 6.7 which in general requires the addition of an acid, such as HCl or preferably $H_3PO_4$ which is less corrosive. This acid added to adjust the pH can be considered all or part of the acid catalyst required for the curing reaction.

In addition to the three requisite components of the padding bath to be used in the process of the invention, there are optional components which may be added, as is well known in the art of textile finishing, to accomplish particular objectives.

Although the process of the invention affords advantageous tactile qualities (hand), further embellishment may be achieved by the use of softeners. These may be, for example, fatty substances such as stearamides, or hydrophobic polymers such as polyethylene emulsions.

Another optional ingredient of the padding composition is a surfactant, or a wetting agent, to aid wetting and penetration of the fibers. Suitable surfactants include alkyl aryl sulfonates and polyoxyethylene derivatives of alkyl phenols (such as "Triton X100", a product of the Rohm and Haas Company).

Another optional ingredient of the padding composition is an additional aminoplast blending ingredient, over and above, but not in place of the requisite amount of DMDHEU. This optional ingredient may be used to increase the degree of durable press character, to impart wet or dry crease angle recovery, and/or to enhance the degree of flame retardancy. Suitable supplementary aminoplast blending ingredients that may be used include methylolureas, methylolmelamines, methylolurons, methyloltriazones, urea, fatty acid amides, ethylene urea, acetamide, dimethyl hydroxymethylcarbamoylethylphosphonate and the methyl ethers of the above listed methylol compounds. The preferred supplementary aminoplast blending ingredients include melamines sold by the American Cyanamid Corporation uner the tradenames: "Aerotex M-3" - tris(methoxymethyl) melamine; "Aerotex 23 Special" — partially methylated pentamethylolmelamine; and "Aerotex UM" — dimethylol melamine. Aother useful supplementary aminoplast blending ingredient is tris-methylol)melamine sold under the tradename "Resloom HP", by the Monsanto Chemical Company.

Another optional ingredient of the padding bath is a peroxygen bleach. Although the process of the invention, without bleach or with a mild after bleach gives quite acceptable color for many uses, we have discovered that for critical applications where extreme whiteness is required, the inclusion of a peroxygen bleach, such as sodium perborate, in the padding bath is highly advantageous. This is a surprising finding which is not known in customary textile mill practice.

According to the prsent process it has also been found that for optimum results between color and durability it is desirable to adjust the pH of the padding formulation containing sodium perborate to between about 5.0 and about 6.7. However, for less critical applications where color formation is of no concern we have found that in the absence of the sodium perborate, optimum durability to repeated laundering is achieved by adjusting the pH between 3 and 5.5.

The solvent most commonly employed for the process of the present invention is water, although it is possible to disperse and apply the reactants and curing catalyst in a non-aqueous solvent such as trichloroethylene, perchloroethylene, methylene chloride, methyl chloroform, or the like. When such a non-aqueous solvent is used, it is often found advantageous to employ enough water to swell the cellulosic textile fibers and thus allow efficient uptake of the reactants. The mixtures of reactants, water, and non-aqueous solvent can be rendered homogeneous by the use of an emulsifier.

The average and preferred amounts (in percentages) by weight, of the various components that can make up the aqueous padding solution of the present invention are provided in Table I below.

The formulation illustrated below in Table I is representative of the present invention. The specific formulation used in treating textiles will depend on the specific end use performance properties and degree of flame retardance desired. This is illustrated in the subsequent examples with cellulosic fabrics and polyester/cotton blends.

TABLE I

COMPOSITION OF FLAME RETARDANT AQUEOUS PADDING BATH SOLUTION

| Component | Solids in Aqueous Solution (%) | Preferred Amount (%) |
|---|---|---|
| Primary Polyol Phosphonate | 10 – 50 | 20 – 40 |
| DMDHEU | 5 – 40 | 8 – 25 |
| Catalyst (including any acid used to adjust pH) | 0.1 – 10.0 | 0.1 – 5.0 |
| Sodium Perborate | 0 – 10 | 0 – 6 |
| Softener | 0 – 3 | 0 – 2 |
| Wetting Agent | 0 – 1 | 0 – 0.5 |

For optimum results, it is preferred to have the ratio of the Primary Polyol Phosphonate to DMDHEU, between about 3:1 and about 1:2.

Although this formulation provided in Table I above is sufficient, additional nitrogen containing resins, i.e., an aminoplast resin in the amount of between 0 and about 30% may be added to further improve the flame retardance, or for increasing the crease recovery properties of the treated material. However these supplementary aminoplasts such as a melamine type may not replace the DMDHEU required for the invention.

The aqueous padding solutions of the present invention are prepared simply by adding the various components together in water. To facilitate solution of the sodium perborate it may be desirable to add the perborate to the above formulation already containing the acid for pH control.

The aqueous solution is placed in a suitable vessel. The flame retardant finish is conveniently applied to the fabric by dipping it into, or passing it through the aqueous bath. The excess liquid is removed by pressing the treated fabric through squeeze rolls, and then the fabric is dried, the temperature being a matter of convenience and equipment ranging from ambient up to the curing temperature. The treated fabric is then heated to cure the finish at temperatures from about 100°C. to about 180°C., and preferably from about 140°C. to about 170°C. These temperatures are used with reaction times ranging from a fraction of a minute to a day, or usually from about 1 to about 10 minutes, depending on temperature used. During the curing of the solution on the fabric, the polyol phosphonate and aminoplast are reacted in situ on the fabric to form a flame retardant finish thereon.

In order to determine the with the and durability of the finish on the fabric, the treated samples are first subjected to a hot water wash cycle in a conventional home washing machine with the water at about 140°F. This is to stimulate an afterwash treatment in a textile mill. In this washing, no soap, detergent, or water hardener is added to the washing cycle.

Then, the samples are subjected to five detergent home laundering cycles in the same washing machine. To each of these cycles there is added a strong detergent such as Proctor and Gamble Corporation's "Tide XK", in the amount of about 50 grams, and 200 parts per million of water hardness (calculated as $CaCO_3$), and 8 bath towels for ballast.

The treated fabric samples may also be tested for their durability by washing them in a boiling aqueous soap-soda solution containing 0.5% soap and 0.2% soda ash ($Na_2CO_3$) for about 3 hours.

After the treated fabric samples have been washed with water, and with detergent, or with a soap and soda ash solution, the fabrics are evaluated for flame retardancy using any of the well known test procedures described hereinbelow. Retention of phosphorus is also measured on some fabrics using X-ray fluoroescence. The various flame retardance tests are described below:

Limiting Oxygen Index (LOI)

The Limiting Oxygen Index (LOI) is a test used for quantitatively measuring the minimum amount of oxygen (in a oxygen-nitrogen mixture) required to sustain combustion. In this test, which is carried out as described in ASTM D-2863, the specimen is ignited from the top, rather than the bottom, and the minimum amount of oxygen required to sustain burning towards the bottom of the specimen is recorded.

Most untreated cotton and blend fabrics require a minimum LOI of 17 to 19% $O_2$ to sustain burning and are considered quite flammable. In general, as reported in Sources & Resources Vol. 2, 1969/5, by R. E. Seaman, increasing the LOI to 21% $O_2$ appears to correlate with fabrics capable of passing the standard horizontal flame test (methenamine pill test) for carpets. Increasing the LOI still further to about 26.5% $O_2$, or greater, represents self-extinguishing properties in air for sample specimens ignited from the bottom in a vertical flame test (i.e. the AATCC 34-1966 flame test described below) which represents the most stringent test conditions commonly used.

In the standard test in air, if the textile is self-extinguishing in the vertical position, it is acceptable for the most stringent applications. If the textile is self-extinguishing in the position of a 45° angle, it is acceptable for many applications. However, if the textile is only self-extinguishing when in a horizontal position the finish is acceptable for use only in less critical applications.

Modified SPI 45° Angle Flame Test

This is another recognized flame testing procedure which is considered more severe than the standard AATCC 33-1966-45° angle test because it entails forced ignition. In this test, like the AATCC 33-1966 flame test, the fabric sample is placed at a 45° angle but the sample is burned or ignited under conditions of forced ignition rather than using a one second timed ignition. For example, an untreated (65/35%) polyester/cotton fabric will pass the AATCC 33-1966-45° angle test whereas it fails to pass the Modified SPI 45° angle test. In the latter case the untreated fabric will burn entirely.

Vertical Flame Test-AATCC 34-1966

In this test, the fabric is suspended vertically with the base of the fabric three-fourths in above a bunsen burner having a flame height of 1½ inches. The flame is held under the sample for 12 second and then withdrawn. Char length is then measured in a standard manner. Char length is the length in inches of charred fabric measured from the base of the fabric upward. Accordingly, a short "char" length of 5 to 7 inches indicates a good flame retardance; whereas a "char" length of 10 to 15 inches indicates a lower degree of flame retardancy of the treated fabric and is not acceptable for most applications.

The present invention will be more fully and completely understood by the following examples.

The following terms, as used herein and in the examples have the following meanings: 5DW - The fabric sample has been given one hot water wash cycle, and five detergent wash cycles.

3.2 oz/yd² - This is a light weight material weighing 3.2 ounces per square yard. Light weight fabrics are generally more difficult to flame retard than heavier weight fabrics.

8 oz/yd² - This is a heavier weight material weighing 8 ounces per square yard.

add-on (%) - This indicates the percent increase in weight of the dry solids applied to the treated fabric based on the weight of the untreated fabric.

OWF - This is used with the term percent add-on, and is defined as "on the weight of the fabric". For example, 20% add-on OWF is equal to 20% solids applied based on the weight of the fabric.

The components utilized in the following examples and tables are set forth in quantities by weight percent of solids or active ingredients.

EXAMPLE 1

A 2.6 ounce per square yard polyester/cotton (65/35%) fabric was padded through an aqueous bath containing the following solids or active ingredients: 30 percent of O,O-diethyl N,N-bis(2-hydroxyethyl)aminomethylphosphonate (Fyrol 6) 13.5 percent of dimethyloldihydroxyethyleneurea (DMDHEU), 1 percent of a softener, a polyethylene emulsion, and 1 percent of zinc nitrate (Catalyst X-4). The pH of the aqueous bath was adjusted to about 5.0 with HCl.

The fabric after being passed through the aqueous bath, was dried for 5 minutes at a temperature of about 230°F., and cured 5 minutes at about 325°F.

The percent dry add-on was calculated to be 27% based on the weight of the untreated fabric. After a one hot water wash, and five detergent wash cycles, the treated fabric was found to self-extinguishing when measured by the Modified SPI-45° Angle Flame Test.

The same fabric untreated burned completely. The LOI of the fabric after the detergent launderings was 24%. The hand of the fabric was soft and flexible.

EXAMPLE 2

A 3.2 oz/yd² cotton print cloth was padded through an aqueous bath containing the following solids or active ingredients: 25 percent of O,O-diethyl N,N-bis(2-hydroxyethyl)aminomethylphosphonate (Fyrol 6), 11.2 percent of DMDHEU, 15 percent Resloom HP, 1 percent part of Catalyst AC, 2.5 percent of phosphoric acid, and 5 percent sodium perborate. The pH of the aqueous bath was 5.8. The dry-on after drying 5 minutes at 230°F. and curing 5 minutes at 300°F., was 40% OWF.

Flame retardancy as measured by the vertical flame test (AATCC 34-1966) showed the treated fabric to be self-extinguishing with a 6 inch char length before and after 5 detergent washes.

No apparent discoloration of the treated fabric was evident.

EXAMPLE 3

To compare the durability to laundering of finishes containing DMDHEU relative to a finish containing another aminoplast resin such as trimethylolmelamine, two aqueous padding baths were made up of compositions as follows:

| Bath (A): | Percent By Weight |
|---|---|
| (C₂H₅O)₂$\overset{O}{\overset{\|}{P}}$CH₂N(CH₂CH₂OH)₂ | 21.6 |
| DMDHEU | 15 |

-continued

| | |
|---|---|
| Zn(NO₃)₂ catalyst | 2 |
| NaHSO₄ (catalyst) | 3 |
| Polyoxyethylene ether (wetting agent) | 0.3 |

Bath B was similar but the DMDHEU was replaced by trimethylolmelamine.

Eight-ounce cotton cloth samples were padded in each bath, dried, cured at 150°, and washed with water. Accelerated laundering was performed by boiling the swatches for 3 hours in a 0.2% soda 0.5% soap solution. The swatch treated with bath composition (A) was found to have 0.9% phosphorus and was selfextinguishing, whereas the swatch treated with bath composition (B) had only 0.27% phosphorus.

EXAMPLE 4

A 3.2 oz/yd² cotton print cloth was padded through an aqueous bath containing the following solids or activity: 30% O,O-diethyl N,N-bis(2-hydroxyethyl)aminomethylphosphonate, 12% of dimethylolethylene urea, 1% Catalyst X-4, and 0.5% Triton X100 with the pH of the formulation adjusted to 5.1 with HCl. The applied solids was 17.7% OWF.

Flame retardancy and durability as measured by the LOI method was 26.8% before washing and 20.2% after 5DW. This shows that a substantial loss in flame retardancy as a result of poor durability of the finish applied to the cotton cloth.

Similar results were also found by modifying the above formulation as follows: 20% of the above primary polyol phosphonate and 25% of the dimethylolethylene urea. Even at this high level of aminoplast, no improvement in durability or flame retardancy after 5DW was found.

EXAMPLE 5

A 3.2 oz/yd² cotton print cloth was padded through an aqueous bath containing the following solids on active ingredients: 30% of O,O-dimethyl N,N-di(2-hydroxypropyl) aminomethylphosphonate, 13.5% DMDHEU, 1% of catalyst X-4, and 0.5% of Triton X 100. The pH was adjusted with hydrochloric acid to 5. The applied solids after drying 5 minutes at 230°F. and curing 5 minutes at 325°F. was 25% OWF.

Flame retardancy as measured by the LOI technique was 26.5% before washing and 21.7% after 5DW. This shows a substantial loss in flame retardancy which is a result of poor durability.

In contrast to the above aqueous bath, a second bath was used which contained a primary polyol phosphonate such as O,O-diethyl N,N-bis(2-hydroxyethyl) aminomethylphosphonate in place of the secondary alcohol phosphate with the same formulation pH, drying and curing conditions. The applied solids resulted in a finish that had excellent durability. The flame retardancy and durability as measured by the LOI method was 26.7% before washing and 25.9% after 5DW.

In Table II, Examples 6 thru 29 illustrate performance of various aqueous baths on 3.2 oz/yd² cotton. The results provided in Table II on durability and/or flame retardancy are based on LOI data as acquired by the test procedure discussed hereinabove.

All of the examples in Table II also contain about 0.5 parts of active Triton X-100 wetting agent. With the exception of Example 29, which was cured at 150°C., all samples were cured at about 163°C.

TABLE II

| (% Solids or Active Ingredients in Padding Bath) | | | | | | | | |
|---|---|---|---|---|---|---|---|---|
| | Examples | | | | | | | |
| | 6 | 7 | 8 | 9 | 10 | 11 | 12 | 13 |
| Fyrol 6 | 40 | 30 | 30 | 30 | 30 | 40 | 30 | 40 |
| DMDHEU | — | — | — | 13.5 | 13.5 | 18 | 13.5 | 18 |
| Aerotex M-3 | — | 12 | — | — | — | — | — | — |
| Aerotex 23 Special | — | — | 12 | — | — | — | — | — |
| Aerotex UM | — | — | — | — | — | — | — | — |
| Resloom HP | — | — | — | — | — | — | — | — |
| Acetamide | — | — | — | — | — | — | — | — |
| Sodium/ perborate | — | — | — | — | — | — | — | — |
| Catalyst (X-4) | 1 | 1 | 1 | 1 | 1 | 1 | — | — |
| Catalyst (AC) | — | — | — | — | — | — | — | — |
| $ZnCl_2$ | — | — | — | — | — | — | — | 1 |
| $MgCl_2$ | — | — | — | — | — | — | — | — |
| Acid for pH Control | — | — | — | HCl | HCl | HCl | $H_3PO_4$ | HCl |
| pH | 7.0 | 6.6 | 6.4 | 5.2 | 5.1 | 5.2 | 5.2 | 5.3 |
| Add-on (%) | 15 | 24 | 29 | 24.8 | 30.7 | 40.5 | 27 | 40.2 |
| LOI (% $O_2$) | | | | | | | | |
| Before washing | 24.9 | 26.7 | 24.4 | 25.8 | 26.7 | 27.1 | 28.5 | 27.2 |
| After 5 DW | 18.5 | 21.0 | 21.0 | 25.0 | 25.9 | 27.3 | 24.7 | 25.0 |
| % Phosphorus | | | | | | | | |
| Before washing | 1.5 | 2.0 | 2.0 | 1.9 | — | 2.5 | — | — |
| After 5DW | .05 | 0.54 | 0.6 | 1.2 | — | 1.5 | — | — |

| | Examples | | | | | | | |
|---|---|---|---|---|---|---|---|---|
| | 14 | 15 | 16 | 17 | 18 | 19 | 20 | 21 |
| Fyrol 6 | 40 | 30 | 30 | 30 | 30 | 30 | 35 | 35 |
| DMDHEU | 18 | 6.75 | 6.75 | 13.5 | 13.5 | 13.5 | 13.5 | 13.5 |
| Aerotex M-3 | — | 6.75 | — | — | 5 | — | — | — |
| Aerotex 23 Special | — | — | 6.0 | — | — | — | — | — |
| Aerotex UM | — | — | — | — | — | — | — | — |
| Resloom HP | — | — | — | 5 | — | 5 | 6 | 6 |
| Acetamide | — | — | — | — | — | — | — | 3 |
| Sodium/ perborate | — | — | — | — | — | — | — | — |
| Catalyst (X-4) | — | 1 | 1 | 1 | 1 | — | — | — |
| Catalyst (AC) | — | — | — | — | — | 1 | 1 | 1 |
| $ZnCl_2$ | — | — | — | — | — | — | — | — |
| $MgCl_2$ | 1 | — | — | — | — | — | — | — |
| Acid for pH Control | HCl | HCl | HCl | HCl | HCl | HCl | HCl | HCl |
| pH | 5.3 | 5.1 | 5.1 | 5.3 | 5.1 | 5.0 | 5.1 | 5.2 |
| Add-on (%) | 38.8 | 20.8 | 20.8 | 30 | 31.0 | 31 | 39 | 36 |
| LOI (% $O_2$) | | | | | | | | |
| Before washing | 28.7 | 29.3 | 26.9 | 27.5 | 28.0 | 30.4 | — | — |
| After 5 DW | 26.2 | 24.9 | 24.9 | 26.8 | 26.9 | 28.5 | 24.8 | 26.2 |
| % Phosphorus | | | | | | | | |
| Before washing | — | — | — | — | — | — | — | — |
| After 5DW | — | — | — | — | — | — | — | — |

| | Examples | | | | | | | |
|---|---|---|---|---|---|---|---|---|
| | 22 | 23 | 24 | 25 | 26 | 27 | 28 | 29 |
| Fyrol 6 | 20 | 20 | 35 | 35 | 30 | 30 | 30 | 30 |
| DMDHEU | 11.2 | 11.2 | 13.5 | 13.5 | 13.5 | 13.5 | 13.5 | 11.2 |
| Aerotex M-3 | — | — | — | — | — | — | — | 8 |
| Aerotex 23 Special | — | — | — | — | — | — | — | — |
| Aerotex UM | 15 | 15 | 6 | 6 | — | — | — | — |
| Resloom HP | — | — | — | — | 5 | 5 | 5 | — |
| Acetamide | — | 3 | — | 3 | — | — | — | — |
| Sodium/ perborate | — | — | — | — | 2 | 5 | 5 | 5 |
| Catalyst (X-4) | — | — | — | — | — | — | — | — |
| Catalyst (AC) | 1 | 1 | 1 | 1 | 1 | 1 | 1 | 1 |
| $ZnCl_2$ | — | — | — | — | — | — | — | — |
| $MgCl_2$ | — | — | — | — | — | — | — | — |
| Acid for pH Control | HCl | HCl | HCl | HCl | $H_3PO_4$ | $H_3PO_4$ | $H_3PO_4$ | $H_3PO_4$ |
| pH | 5 | 5 | 4.8 | 4.9 | 5.7 | 6.6 | 5.0 | 6.0 |
| Add-on (%) | 38 | 36 | 42 | 42 | 35 | 35 | 38 | 25 |
| LOI (% $O_2$) | | | | | | | | |
| Before washing | 28.6 | 30.1 | — | — | — | — | — | 29.3 |
| After 5 DW | 26.5 | 27.7 | 25.7 | 26.6 | 25.6 | 24.8 | 26.3 | 28.0 |
| % Phosphorus | | | | | | | | |
| Before washing | — | — | — | — | — | — | — | — |
| After 5DW | — | — | — | — | — | — | — | — |

In Table II, Examples 6 through 8 illustrate that when (O,O-diethyl N,N-bis(2-hydroxyethyl)aminomethyl-phosphonate (Fyrol 6) is applied alone or in combination with Aerotex M-3 or Aerotex 23 Special, and an acid catalyst, the finish on the fabric is not self-extinguishing by even the most lenient test after 5 DW and is not durable to washing. At most, about 30% phosphorus is retained. The lack of durability of the finished fabrics after being washed is also shown by the low LOI results of about 18 to 21.

Examples 9 through 11 illustrate that durability to laundering is improved considerably at various add-on levels when the pH is adjusted to about 5.0 and about 2.2 parts of Fyrol 6 is used for each part of DMDHEU solids.

Examples 12 through 14 illustrate that a less corrosive acid such as phosphoric acid and other acid catalysts such as zinc chloride or magnesium chloride may be used.

Examples 15 and 16 show that when half of the melamine type resin, especially Aerotex 23 Special as used in Examples 7 and 8, is replaced with DMDHEU, the degree of flame retardancy before laundering is improved even at somewhat lower add-on levels.

Examples 17 through 25 show that the degree of flame retardancy before or after laundering can be improved still further by adding melamine type resins alone or in combination with acetamide to the DMDHEU. The Fyrol 6 content can also be reduced to as low as 20% in the padding bath.

Examples 26 through 28 show that with sodium perborate in the formulation, durability after laundering improves with a decreasing pH, i.e., from 6.6 down to 5.0. With regard to color, 2 parts of sodium perborate was insufficient in preventing color development. However, with 5 parts of sodium perborate, the color was improved considerably and essentially non-existent at the higher pH of 6.6, as in Example 27. Residual color from Example 27 was removed after soaking the sample for 1 minute in a 5% solution of sodium perborate at 180°F.

Example 29, which was formulated at a pH of 6 and cured on the fabric at 150°C., was found to have excellent color, high degree of flame retardancy and a soft hand.

In Table III below, additional Examples 30 through 36 are provided to illustrate the durable flame retardant properties with the use of other primary polyol phosphonates in combination with dimethyloldihydroxyethylene urea (DMDHEU). As in Examples 6 through 29 of Table II, the examples in Table II contain about 0.5 parts of active Triton X-100 wetting agent.

TABLE III

| | Examples | | | | | | |
|---|---|---|---|---|---|---|---|
| | 30 | 31 | 32 | 33 | 34 | 35 | 36 |
| $(C_2H_5O)_2-P(O)-N(C_2H_4OH)_2$ | 30 | — | — | — | — | — | — |
| $OCH_2C(CH_3)_2CH_2OP(O)CH_2N(C_2H_4OH)_2$ | — | 30 | — | — | — | 30 | 30 |
| $[(CH_3)_2CHO]_2-P(O)-CH_2N(C_2H_4OH)_2$ | — | — | 30 | — | — | — | — |
| $(C_2H_5O)_2-P(O)-CH_2CH_2C(O)N(C_2H_4OH)_2$ | — | — | — | 30 | — | — | — |
| $(C_2H_5O)_2-P(O)-CH_2C(O)N(C_2H_4OH)_2$ | — | — | — | — | 30 | — | — |
| DMDHEU | 13.5 | 13.5 | 13.5 | 13.5 | 13.5 | 13.5 | 13.5 |
| Tris(methoxymethyl)melamine | — | — | — | — | — | 8 | 8 |
| Catalyst (X-4) | 1 | 1 | 1 | 1 | 1 | — | 1 |
| Catalyst (AC) | — | — | — | — | — | 1 | — |
| Acid | HCl | HCl | HCl | HCl | HCl | HCl | HCl |
| pH | 5.5 | 5.0 | 5.0 | 5.0 | 6.0 | 5 | 5 |
| Add-on (%) | 31 | 28.6 | 21 | 27.6 | 27.6 | 40 | 40 |
| LOI | | | | | | | |
| Before washing | 27 | 30.5 | 26.3 | 28.3 | 29.0 | 27.5 | 27.5 |
| After 5 DW | 23.9 | 27.8 | 23.1 | 25.6 | 23.4 | 26.4 | 25.8 |

To illustrate the connection in flame retardancy between LOI and vertical char length, some samples were also tested by the vertical flame test, AATCC 34-1966, before and after 5 detergent washings. The char length of samples of the various Examples tabulated below in Table IV, further illustrates the relationship described hereinabove.

TABLE IV

| Sample No. | Char Length Before Washing | Char Length After 5 Detergent Washings |
|---|---|---|
| 19 | 5.5 | 5.75 |
| 22 | 6.5 | 6.0 |
| 23 | 6.0 | 6.25 |
| 25 | 6.0 | 6.0 |
| 35 | 5.0 | 7.75 |
| 36 | 5.5 | 5.5 |

As can be seen from the results of these various examples the retention of the char length after washing is not greatly affected.

In addition to providing flame retardancy, durability and good color of treated textiles, it is also intended to provide a soft hand. Primary polyol phosphonates reacted with 12 parts of a melamine type resin result in a rather firm hand. However, similar fabrics containing 13.5 parts of DMDHEU or a blend of about 11 to 13.5 parts of DMDHEU and a melamine resin as in Example 29 result in finished fabrics with a soft hand.

EXAMPLE 37

This example illustrates the preparation of:

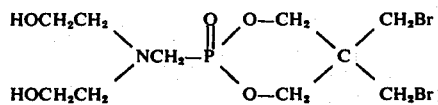

Equimolar proportions of 2,2'-bis-bromomethyl-1,3-propanediol and diethyl phosphite are heated at 100°C. over a period of 2 days while removing the ethanol by-product so as to yield a viscous liquid phosphonate having the formula:

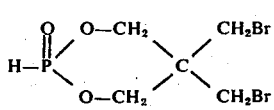

This intermediate is then treated with an equimolar quantity of hydroxyethyl oxazolidine while under agitation and while being maintained at a temperature below 45°C. thereby yielding the compound whose formula is depicted hereinabove. This end product had the following analysis, Found: Br=35.1%, N=3.4%, P=8.8%; Theoretical: Br=36.8%, N=3.22%, P=7.13%.

EXAMPLE 38

This example illustrates the preparation of:

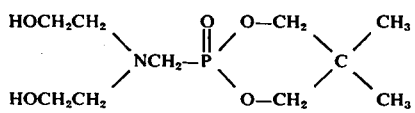

A total of 234 grams of hydroxyethyl oxazolidine is placed into a reactor to which there is then slowly added, under agitation, a total of 310 grams of the cyclic phosphonate of 2,2-dimethylpropane-1,3-diol. The system reached a temperature of 53°–54°C. and the reaction was complete in 2-½ hours. The resulting product is obtained in a purity of about 95% and has a refractive index $n_D^{25} = 1.4900$.

EXAMPLE 39

This example illustrates the preparation of:

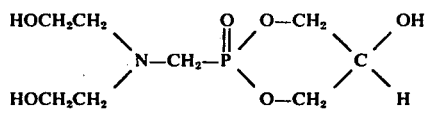

A total of 224 grams of hydroxyethyl oxazolidine is heated to 60°C. whereupon 274 grams of the cyclic phosphonate of glycerol are slowly added with agitation. The system is cooled to maintain its temperature at 60°–70°C. The reaction is complete after a total of about two hours and the resulting reaction product contained a substantial proportion of the above described compound along with some linear dimers or polyesters thereof.

It is apparent that many modifications and variations of the invention as hereinbefore set forth may be made without departing from the spirit and scope thereof; and therefore, only such limitations should be imposed as are indicated in the appended claims.

What is claimed is:

1. The compound:

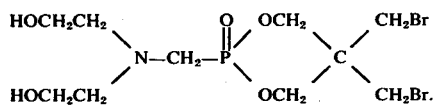

2. The compound:

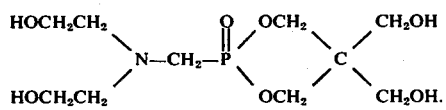

3. The compound:

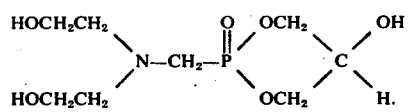

* * * * *